United States Patent
Ellington et al.

(10) Patent No.: US 9,298,879 B2
(45) Date of Patent: Mar. 29, 2016

(54) METHOD AND SYSTEM FOR COLLECTION AND MANAGEMENT OF PERIOPERATIVE DATA

(71) Applicants: Kenneth Ellington, Asheville, NC (US); Robert O'Brien, Asheville, NC (US); James Hurst, Asheville, NC (US)

(72) Inventors: Kenneth Ellington, Asheville, NC (US); Robert O'Brien, Asheville, NC (US); James Hurst, Asheville, NC (US)

(73) Assignee: Kenneth Raynor Ellington, Asheville, NC (US)

( * ) Notice: Subject to any disclaimer, the term of this patent is extended or adjusted under 35 U.S.C. 154(b) by 192 days.

(21) Appl. No.: 13/956,819

(22) Filed: Aug. 1, 2013

(65) Prior Publication Data

US 2015/0039339 A1 Feb. 5, 2015

(51) Int. Cl.
*G06F 12/00* (2006.01)
*G06F 19/00* (2011.01)

(52) U.S. Cl.
CPC .......... *G06F 19/322* (2013.01); *G06F 19/3481* (2013.01)

(58) Field of Classification Search
CPC ............................ G06F 19/322; G06F 19/3481
See application file for complete search history.

(56) References Cited

U.S. PATENT DOCUMENTS

2013/0254697 A1* 9/2013 Bush et al. .................... 715/771

OTHER PUBLICATIONS

"The Electronic Anesthesia Record: CPA", Brutane, vol. 1, Issue 3, The Department of Anesthesiology at the University of Tennessee in Knoxville, Fall 2010—10pages.
CRNAbiz compilers, "iPad™ Jumps into the Anesthesia Digital Divide", www.crnabiz.com/side/content/ipad™-jumps-anesthesia-digital-divide, Dec. 17, 2012—4 pages.

* cited by examiner

*Primary Examiner* — Yong Choe
(74) *Attorney, Agent, or Firm* — Dority & Manning, P.A.

(57) ABSTRACT

Methods and systems for collecting and managing anesthesia perioperative data of a patient are provided. More particularly, a method of the present disclosure can include presenting a dashboard view of a user interface on a display of a computing device. The dashboard view can display a plurality of modules corresponding to the various perioperative periods of a procedure. In response to a user input, the method can access a module in the plurality of modules if it is determined that the user has access to the module, and can present a corresponding module interface.

10 Claims, 12 Drawing Sheets

| Procedure & Plan | Preoperative Assessment: Airway Exam | + |

Medications & Allergies

Past Surgery — Neck Range of Motion [Full] [Limited] [Other]
(if other) _____

Airway, Head, & Neck — Hyomental Distance (fingers) [1] [2] [3] [4] [4+]

Cardiovascular — Mallampati Score [1] [2] [3] [4]

Endocrine/Renal — Teeth

Gastrointestinal — Teeth Notes

Hematologic

Mental Status, Other — [No] [Yes] Dentures  [No] [Yes] Caps/Crowns  [No] [Yes] Missing Teeth Neuromuscular/Skeletal — [No] [Yes] Loose/Chipped Teeth Respiratory — Hearing Test Results — [No] [Yes] Hard of Hearing  [No] [Yes] Hearing Aid Signature/Close Case pheral Block Account Login | Workflow Management | Case Data | Continuous Monitoring | Code Case | Account Administration

FIG. 4

Immediate Pre-Operative Assesment

| No | Yes | Patient has been determined to be an appropriate candidate for anesthesia |
| No | Yes | Previous evaluation and recent lab work reviewed | No | Yes | No changes in above examination |
| No | Yes | Current infection present |

Remarks

Provider Name:

Anesthesiologist signature has NOT been captured for this case.

Clear  Sign  Print  Close pheral Block

Account Login | Workflow Management | Case Data | Continuous Monitoring | Code Case | Account Administration

Post Anesthesia Assessment

Patient Name: Patient567, Test  Procedure: Laproscopic Appendectomy  Date of Service: 2013-03-21
Patient DOB: 1955-12-15  Patient MR#: 45637365  Patient Gender: Male

[No] [Yes] Anesthesia Complications  [No] [Yes] Airway Patent  [No] [Yes] N/V

Hydration Status  [Satisfactory] [Unsatisfactory]

Pain Score  Cardiac Rhythm

Provider Name:

pheral Block

Anesthesiologist signature has NOT been captured for this case.

[Clear]  [Sign]  [Print]  [Close]

Account Login  Workflow Management  Case Data  Continuous Monitoring  Code Case  Account Administration

Anesthesia Quality Improvement

| | | |
|---|---|---|
| No Yes | Anesthetic complications occurred | |
| No Yes | Significant delay | No Yes Extended PACU stay |
| No Yes | Case cancelled | No Yes Unanticipated hospital admission |
| No Yes | Equipment problem | No Yes Unanticipated ICU admission |
| No Yes | Death | No Yes Incorrect surgical site |
| No Yes | Vascular access complication | No Yes Cardiac Arrest |
| No Yes | Incorrect Patient | No Yes Infection after regional anesthesia |
| No Yes | Perioperative MI | No Yes Intraoperative awareness |
| No Yes | Epidural hematoma | No Yes Anaphylaxis |
| No Yes | Unrecognized difficult airway | No Yes High spinal |
| No Yes | Malignant hypothermia | No Yes Unplanned reintubation |
| No Yes | Post puncture headache | No Yes Transfusion reaction |

Account Login | Workflow Management | Case Data | Continuous Monitoring | Code Case | Account Administration pheral Block

HCAHPS Patient Satisfaction Survey

No | Yes | Did the anesthesiologist treat with courtesy and respect?
No | Yes | Did the anesthesiologist listen carefully to you?
No | Yes | Did the anesthesiologist explain things in a way you could understand?

How would you rate your anesthesiologist on a scale of 1 to 10?

| 1 | 2 | 3 | 4 | 5 | 6 | 7 | 8 | 9 | 10 |

Provider Name:

Anesthesiologist signature has NOT been captured for this case.

Clear | Sign | Print | Close

Account Login | Workflow Management | Case Data | Continuous Monitoring | Code Case | Account Administration pheral Block

Procedure | Peripheral Nerve Block: Immediate Pre-Block Assessment General Information
Consent
Agents & Vitals
Peripheral Nerve Block
Block 1
Block 2
Sign & Close Procedure Performed in [Block room] [O.R.] [PACU] [Other]
Other location:
Surgery Date [ ] Surgery Time [ ]
[No][Yes] Changes in Lab/ECG/CXR?
BP [ ] P [ ] SpO2 [ ] RR [ ] LOC [ ]
Pre-Block Pain Score [ ] Block for Post-op Pain Relief ordered by Dr:
[No][Yes] Allergies
Diagnosis:
Surgery:

pheral Block

Account Login | Workflow Management | Case Data | Continuous Monitoring | Code Case | Account Administration

METHOD AND SYSTEM FOR COLLECTION AND MANAGEMENT OF PERIOPERATIVE DATA

FIELD

The present disclosure relates generally to a method and system for collection and management of anesthesia perioperative data.

BACKGROUND

Surgical procedures during which the patient requires anesthesia involve various stages, including preoperative stages, intraoperative stages, and postoperative stages. During each of these various stages, it can be important that accurate and complete information associated with the patient is collected and available to the anesthesiologists, certified registered nurse anesthetists (CRNA), and other medical professionals. Accordingly, various systems are currently used to collect a patient's information at the various stages of the procedure. For example, a CRNA may collect certain information associated with the patient prior to the surgery using a first system, then an anesthesiologist may collect certain information associated with the patient immediately prior to the surgery using a second, different system, and so on and so forth.

However, certain problems can exist with such a method. For example, certain preoperative data associated with the patient collected using the first system may need to be recollected using the second system. Additionally, it can be difficult to ensure that all the required information associated with the patient has been entered prior to moving on to the next stage in the procedure. Accordingly, a method for collecting and managing perioperative data regarding a patient throughout the patient's procedure would be beneficial. Moreover, a method for determining whether or not all required information from one or more previous stages of the procedure has been collected would be particularly useful. Further, a user interface that can provide a user intuitive method for collecting the data would be particularly beneficial.

SUMMARY

Aspects and advantages of the invention will be set forth in part in the following description, or may be obvious from the description, or may be learned through practice of the invention.

In one exemplary aspect of the present disclosure, a computer-implemented method of collecting anesthesia perioperative data of a patient associated with a case is provided. The method includes presenting a dashboard view of a user interface on a display of a computing device. The dashboard view displays a plurality of modules. The plurality of modules is displayed in a sequential manner corresponding to a sequential order of perioperative periods. The method also includes receiving a user input accessing a first module of the plurality of modules. In response to the user input, the method includes determining whether the user has access to the module based on completion of one or more previous modules in the sequential order. Additionally, the method includes presenting a first module interface associated with the first module when it is determined that the user has access to the first module.

In another exemplary embodiment of the present disclosure, a mobile computing device is provided including a display device, one or more processors, and at least one tangible non-transitory computer-readable medium. The computer-readable medium stores instructions that when executed by the processor causes the processor to perform operations. The operations include presenting a dashboard view of a user interface on a display of a computing device. The dashboard view displays a plurality of modules. The plurality of modules is displayed in a sequential manner corresponding to a sequential order of perioperative periods. The operations also include receiving a user input accessing a first module of the plurality of modules. The first module configured to receive anesthesia perioperative data of a patient. Additionally, in response to the user input, the operations include determining whether the user has access to the first module based on completion of one or more previous modules in the sequential order. Further, the operations include presenting a first module interface associated with the first module when it is determined that the user has access to the first module.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 3 depicts an exemplary preoperative evaluation module interface in accordance with an exemplary embodiment of present disclosure.

FIG. 4 depicts an exemplary immediate preinduction evaluation module interface in accordance with an exemplary embodiment of present disclosure.

FIG. 6 depicts an exemplary postoperative evaluation module interface in accordance with an exemplary embodiment of present disclosure.

FIG. 7 depicts an exemplary surgical care improvement plan evaluation module interface in accordance with an exemplary embodiment of present disclosure.

FIG. 9 depicts an exemplary patient satisfaction report module interface in accordance with an exemplary embodiment of present disclosure.

FIG. 10 depicts an exemplary nerve block module interface in accordance with an exemplary embodiment of present disclosure.

DETAILED DESCRIPTION

Figure 1:
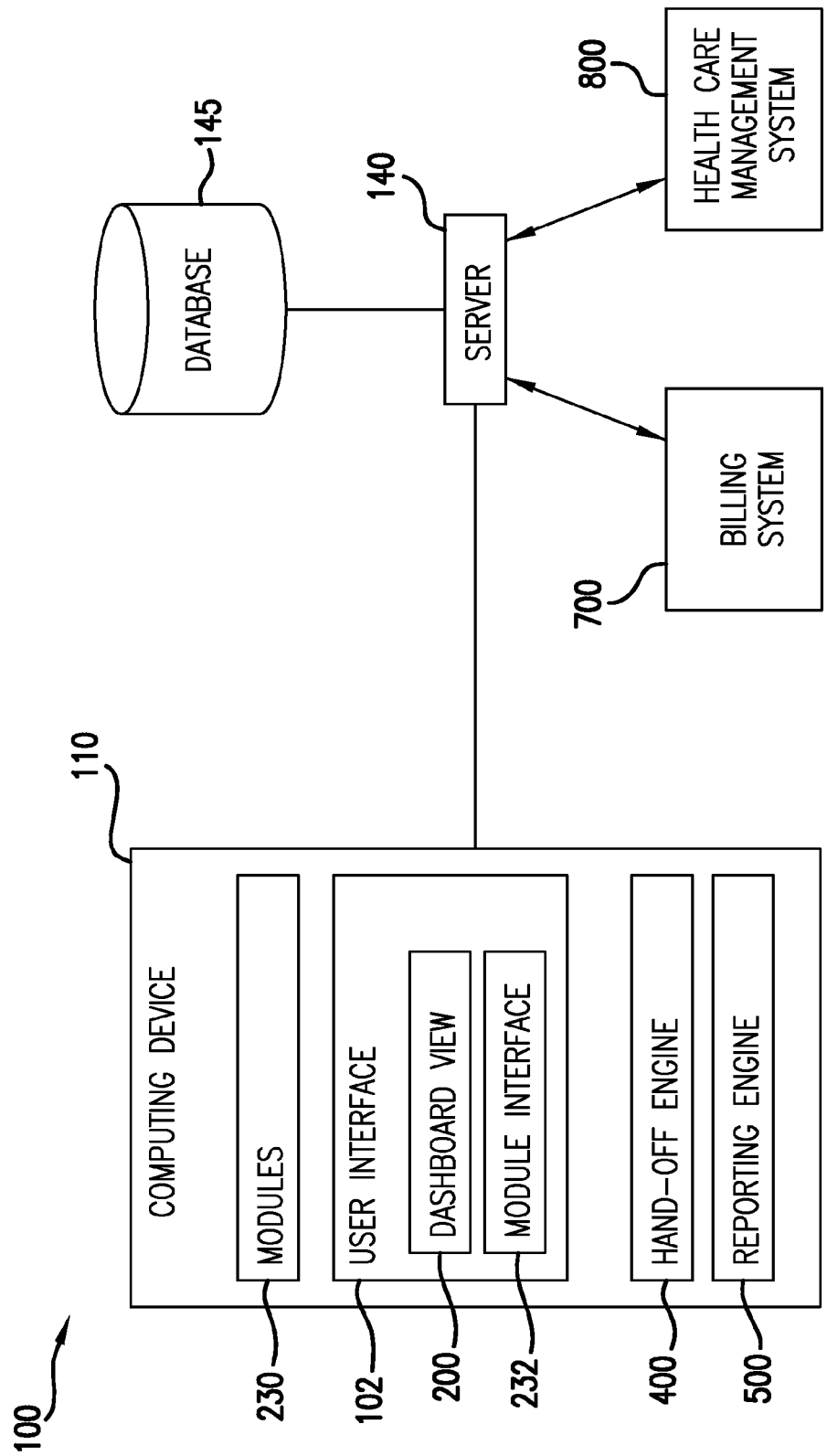
FIG. 1 depicts a block diagram illustrating the operation of an exemplary system for collecting and managing anesthesia perioperative data of a patient according to an exemplary embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Overview

Generally, the present disclosure is directed to a method and system for collecting and managing anesthesia perioperative data of a patient undergoing a procedure. More particularly, the present disclosure provides an integrated computer-implemented method of collecting and managing the patient's anesthesia perioperative data throughout the patient's procedure. For example, the method and system of the present disclosure can collect and manage the patient's preoperative data, the patient's intraoperative data, and the patient's postoperative data.

In one exemplary aspect, the method can include presenting a dashboard view of a user interface on a display of a computing device. The dashboard view can display a plurality of modules in a sequential manner corresponding to a sequential order of perioperative periods of the patient's procedure. Each module in the plurality of modules can be configured to receive a user input corresponding to certain anesthesia perioperative data of the patient and associated with the particular perioperative period of which the particular module corresponds. The modules can also be configured to store the received anesthesia perioperative data in a memory of the computing device.

Accordingly, a user input can be received to access a first module in the plurality of modules. In response to the user input, the method can include determining whether the user has access to the module based on the completion of one or more previous modules in the sequential order. More particularly, the method can include verifying that all previous modules in the plurality of modules, based on the sequential order in which they are displayed, have been completed prior to allowing the user to access the first module. Once verified, a first module interface can be presented. The anesthesia perioperative data of the patient required for the particular perioperative period and associated with the first module can be entered by the user via the first module interface.

Once it has been determined that all required data associated with the first module has been received, the dashboard view of the user interface can again be displayed, along with a signal to indicate that the first module has been completed. The described steps can be repeated for each subsequent module in the plurality of modules until all of the required modules have been completed. Such an exemplary method can ensure that all required anesthesia perioperative data of a patient is received by preventing the user from accessing subsequent modules until all required data has been collected for the required previous modules. Additionally, the above exemplary method can check the data against various rules to ensure that the collected data satisfies any necessary requirements, such as billing requirements, health care regulatory requirements, etc.

The exemplary method described can provide a more efficient and user intuitive environment for collecting and managing the anesthesia perioperative data of the patient. Additionally, in one exemplary embodiment, the exemplary method described can be implemented on a handheld computing device, such as a tablet. Such a device can have a touch screen display providing visual feedback to the user as the user collects the required data using, for instance, touch interaction with the display. The user intuitive interface combined with easy to use touch interactions can enhance the experience of the user.

In another exemplary embodiment, the plurality of modules can include the following modules and can display the modules in the dashboard view in the following sequential order: (1) a preoperative evaluation module, (2) an immediate preinduction evaluation module, (3) a procedure module, (4) a postoperative evaluation module, (5) an anesthesia quality improvement module, (6) a surgical care improvement plan evaluation module, and (7) a patient satisfaction report module.

In still another exemplary aspect, the method and system of the present disclosure can include generating and providing one or more reports compiling data collected and received in association with a particular patient, or a plurality of patients. Additionally, subsequent to completion of all required modules, the method can include providing the collected anesthesia perioperative data of a patient to one or more remote systems, such as a billing system or a heath care management system.

In yet another exemplary aspect, the method can ensure the user is in compliance with policies limiting the amount of patients the particular user is allowed to manage. For example, a hospital or health care provider may limit the amount of patients an anesthesiologist is allowed to manage at a particular time. Accordingly, the method can access the user information associated with the professional to determine if the anesthesiologist has the capacity to manage or oversee the administration of anesthesia to the patient. The user information can include the number of cases currently being handled by the professional. Similarly, a hospital or health care provider may limit the amount of patients a certified registered nurse anesthetist (CRNA) can manage. Therefore, the method can also access the user information associated with the professional to determine if the CRNA has the capacity to manage the patient. In either of the above examples, the method can allow the user or an administrator to "hand-off" the patient to a different anesthesiologist or CRNA so as to more effectively manage the case loads.

System for Collecting and Managing Anesthesia Perioperative Data

With reference now to the FIGS., exemplary embodiments of the present disclosure will now be discussed in detail. FIG. 1 depicts a block diagram illustrating certain aspects of an exemplary system 100 for collecting and managing anesthesia perioperative data. The system 100 of FIG. 1 generally includes a user interface 102 implemented using a computing device 110. The details of the computing device 110 will be discussed in greater detail with reference to FIG. 12. In one exemplary embodiment, however, the exemplary user interface 102 can be implemented using a handheld computing device, such as a tablet. In such an embodiment, the tablet can include a touch screen display for presenting the different views of the user interface 102 (see FIGS. 2-10) and for receiving a user input, such as a touch interaction with the display.

The exemplary user interface 102 can present a dashboard view 200. The dashboard view 200 can display a plurality of sequential modules 230 corresponding to various perioperative periods of the patient's surgery. From the dashboard view 200, a user can access a module using a corresponding module interface 232. Additionally, a method for collecting and managing anesthesia perioperative data of a patient can be implemented through the user interface 102 using the dashboard view 200 and the module interfaces 232. As will be discussed in greater detail with reference to FIG. 11 below, the method can allow a user to collect data from each perioperative period of the patient's procedure by intuitively and sequentially progressing through the respective perioperative modules as they are presented in the dashboard view 200 of the user interface 102.

Additionally, the computing device 110 can include a hand-off engine 400 configured to allow a user to transfer his or her management of a patient to another user. More particularly, the hand-off engine 400 can access information associated with the user to determine whether the user has authorization to access the patient's case as a manager. In one exemplary embodiment, the user can be an anesthesiologist assigned to manage or oversee the patient and/or administer the anesthesia to the patient. In another embodiment, the user can be a CRNA assigned to manage the patient. Notably, certain hospitals or health care providers may limit the amount of patients a particular anesthesiologist is authorized to manage, and/or may limit the amount of patients a CRNA is authorized to manage. By way of example only, in certain exemplary embodiments, an anesthesiologist may be limited to managing four patients at a time and a CRNA may be limited to managing one patient at a time. It should be appreciated, however, that in other exemplary embodiments, a hospital or health care provider may allow an anesthesiologist to manage more than four patients at a time and may allow a CRNA to manage more than one patient at a time.

Accordingly, the hand-off engine 400 can be configured to access information associated with a user and determine whether the user has authorization to access the case as a manager. In one exemplary aspect, the hand-off engine 400 can access information associated with a user stored in a memory of the computing device 110 and/or communicated to the computing device 110 by a server 140. In such an embodiment, the hand-off engine 400 can determine how many other patients the user is managing and compare that number to a predefined limit to determine whether the user has authorization to access the case as a manager.

If a user does not have authorization to access the case as a manager, or for any other reason, the hand-off engine 400 can allow the user to "hand-off" the case to another user. At such a point, the hand-off engine 400 can change certain information associated with the user such that a new user (i.e., a new anesthesiologist or new CRNA) has access to the case as a manager. For example, a first anesthesiologist can hand-off the patient to a second anesthesiologist or a first CRNA may hand-off the patient to a second CRNA.

In certain exemplary embodiments, the hand-off engine 400 can be implemented by the user interface 102, through the computing device 110, in response to a user input. In other exemplary embodiments, the hand-off engine 400 can be implemented in response to an input by an authorized administrator, such as a hospital manager, to hand-off a patient's case to a different anesthesiologist or CRNA at any point during the patient's procedure. Such functionality can allow the authorized administrator to efficiently manage the patient case load of the available anesthesiologists and CRNAs.

Still referring to FIG. 1, the computing device 110 can further include a reporting engine 500 configured to generate and provide or communicate one or more reports to a display of the computing device 110 or to a server 140. More particularly, the reporting engine 500 can generate and provide or communicate one or more reports related to the collected anesthesia perioperative data of the patient. Such reports can be generated subsequent to the collection of all the required anesthesia perioperative data of the patient, or at any suitable time during the collection of the anesthesia perioperative data. Additionally, the reporting engine 500 can access and generate reports relating to the anesthesia perioperative data associated with a plurality of patients stored on the computing device 110 and/or communicated by the remote server 140. Further, the one or more reports can be provided automatically after the occurrence of a certain event, or in response to a user input to the user interface 102.

For the exemplary embodiment of FIG. 1, as shown, the computing device 110 is in communication with a server 140, which is in communication with a database 145. The database 145 can allow for storage of data communicated with the server 140, such as anesthesia perioperative data collected using the computing device 110. In certain embodiments, the database 145 can be split up so that it is located in multiple locations.

Additionally, the server 140 can share data with a billing system 700 and a health care management system 800. This functionality can have various benefits. For example, more efficient and accurate patient billing information can be communicated to the appropriate parties, as in some instances the billing amount to the patient varies depending on the quality of the anesthesia perioperative data collected. Additionally, certain of the anesthesia perioperative data collected can be communicated to, for instance, a hospital's pharmacy to help the pharmacy manage inventory.

It should be appreciated, however, that in other exemplary embodiments of the present disclosure, the billing system 700 and/or health care management system 800 can be incorporated into the server 140, or the server may not be in communication with one or either of the billing system 700 and/or health care management system 800. Additionally, in still other exemplary embodiments, the computing device 110 may not be in communication with a server 140 and can be a stand-alone device.

The User Interface

Referring now to FIGS. 2-10, an exemplary dashboard view 200 and exemplary module interfaces, as presented by the user interface 102 of the system 100, are provided. The user interface 102 disclosed herein can provide a more efficient, user-friendly and intuitive environment for collecting and managing the anesthesia perioperative data of a patient. For example, the user interface disclosed herein can provide a sensory feedback to the user regarding the user's progress towards satisfaction of a condition that is required to complete the collection of all required anesthesia perioperative data.

Figure 2:
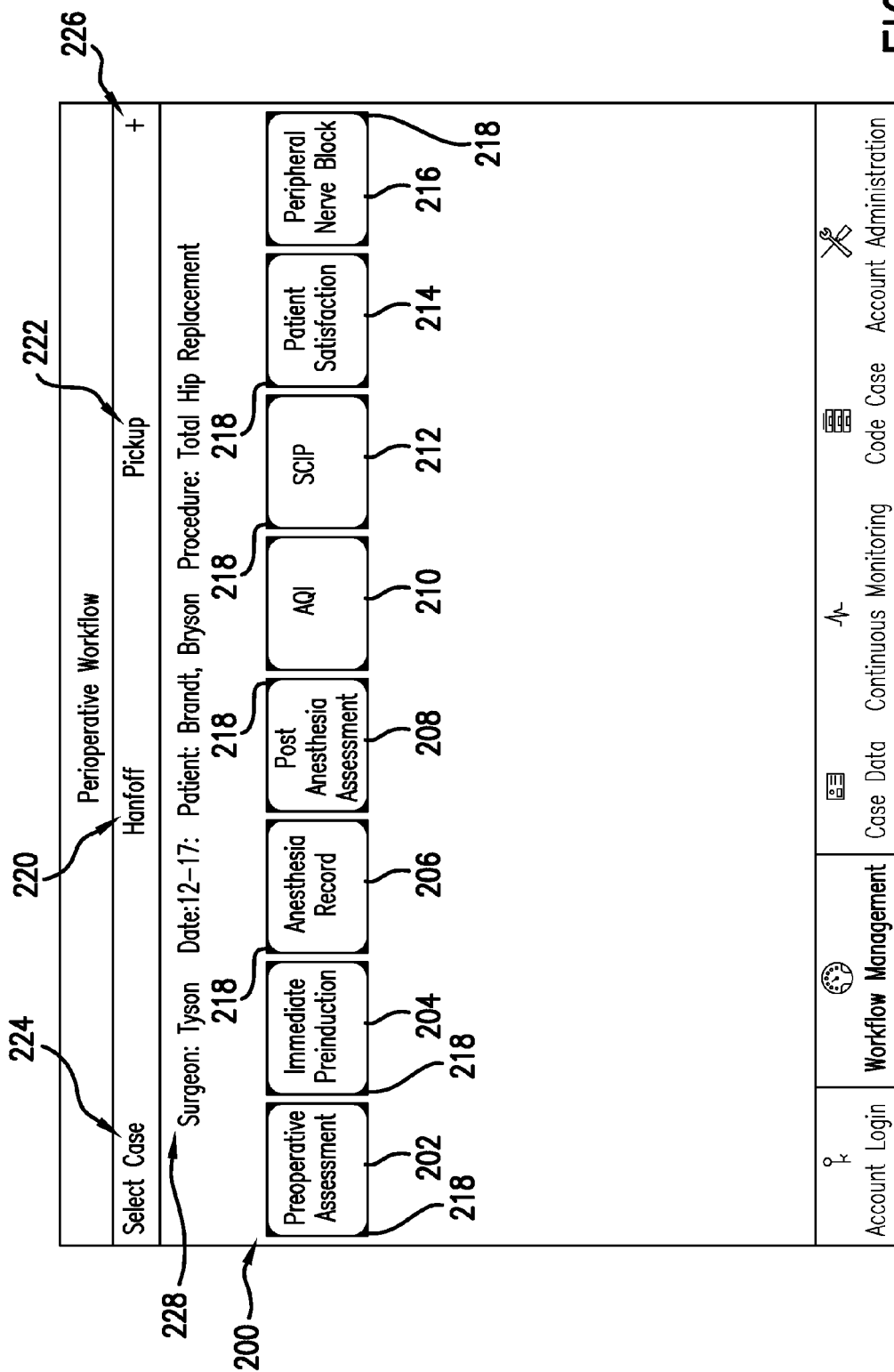
FIG. 2 depicts an exemplary dashboard view of an exemplary user interface in accordance with an exemplary embodiment of present disclosure.

Referring specifically to FIG. 2, an exemplary embodiment of a dashboard view 200 presented by the user interface 102 is provided. As shown, the exemplary dashboard view 200 displays a plurality of modules in a sequential manner corresponding to the sequential manner in which they generally must be completed. For the exemplary embodiment of FIG. 2, the plurality of modules are displayed in the exemplary dashboard view 200 in the following order and must be completed in the following order: first the preoperative evaluation module 202, second the immediate preinduction evaluation module 204, third the procedure module 206, fourth the postoperative evaluation module 208, fifth the anesthesia quality improvement (AQI) module 210, sixth the surgical care improvement plan (SCIP) evaluation module 212, and seventh the patient satisfaction report module 214. The exemplary embodiment of FIG. 2 additionally includes a peripheral nerve block module 216 displayed at the end of the plurality of modules. As will be discussed with reference to FIG. 10, however, the peripheral nerve block module 216 is optional, and if required, can be completed after the preoperative evaluation module 202.

As shown in FIG. 2, a plurality of indicia can be presented in the dashboard view 200 of the user interface 102. For the exemplary embodiment of FIG. 2, each indicia in the plurality of indicia corresponds to a module in the plurality of modules. Further, each indicia includes a colored portion 218 extending around a periphery of the corresponding module. The colored portion 218 can be configured to indicate to the user whether the corresponding module has been completed. For example, the colored portion 218 can be a green color when the module has been completed and can be a red color when the module is incomplete. Such a configuration can indicate to the user their progress in completing the collection of the required anesthesia perioperative data of the patient, as well as indicate to the user the next appropriate contact point on, for instance, the display of the computing device to touch to continue collecting the required anesthesia perioperative data of the patient.

With continued reference to FIG. 2, the dashboard view 200 additionally allows a user to manage his or her workload. More specifically, as previously discussed, a hospital or health care provider can limit the amount of patients, or cases, an anesthesiologist or CRNA manages. Accordingly, the exemplary dashboard view 200 of the user interface includes a "Handoff" function 220. The handoff function 220 can access the handoff engine 400 previously discussed with reference to FIG. 1. As discussed, the handoff engine 400 can allow a user, such as an anesthesiologists or CRNA, to handoff the patient to a different user. In such an embodiment, the patient can then be sent or assigned to the new user, either on the same computing device or on a different computing device. The new user can then accept responsibility for the patient using a "Pickup" function 222. The exemplary dashboard view 200 also includes functions to add a new case/patient 226 and to select a case/patient amongst one or more cases 224.

Referring now to FIG. 3, an exemplary Preoperative Assessment or Evaluation module interface 240 is provided. The module interface 240 allows a user to access or interact with the preoperative assessment module 202. The module 202 can be completed first, and thus no previous modules are required to be completed before a user can have access. The module 202 can collect data associated with the patient in preparation for a procedure. For example, the module 202 can collect information including the patient's demographics, insurance information, health history, etc. The data can be collected by the user's touch interaction with the display of the computing device via the preoperative assessment module interface 240 provided in FIG. 3. In such an embodiment, the user can be, for example, an anesthesiologist, a CRNA, an administrative person, the patient, etc. It should be appreciated, however, that in other exemplary embodiments, some or all of the required data may be imported from a patient's file or from a questionnaire filled out by the patient electronically and communicated to the computing device 110 by, for instance, a remote server.

FIG. 4 provides an exemplary immediate preinduction evaluation module interface 242. The module interface 242 allows a user to access or interact with the immediate preinduction evaluation module 204. The module 204 can be accessed after the preoperative evaluation module 202 has been completed. However, if it is determined that the patient may require a nerve block, then the nerve block module 216, discussed below, may be required to be completed prior to the immediate preinduction evaluation module 204. While the immediate preinduction evaluation module interface 242 is presented on the display of the computing device 110 by the user interface 102, a user can collect data that can indicate whether or not the patient is cleared to receive anesthesia. In one embodiment, the user can be the anesthesiologist overseeing the administration of anesthesia to the patient. Additionally, or alternatively, some or all of the information required by module 204 can be collected by accessing the patient's data collected in any of the previous modules.

Figure 5:
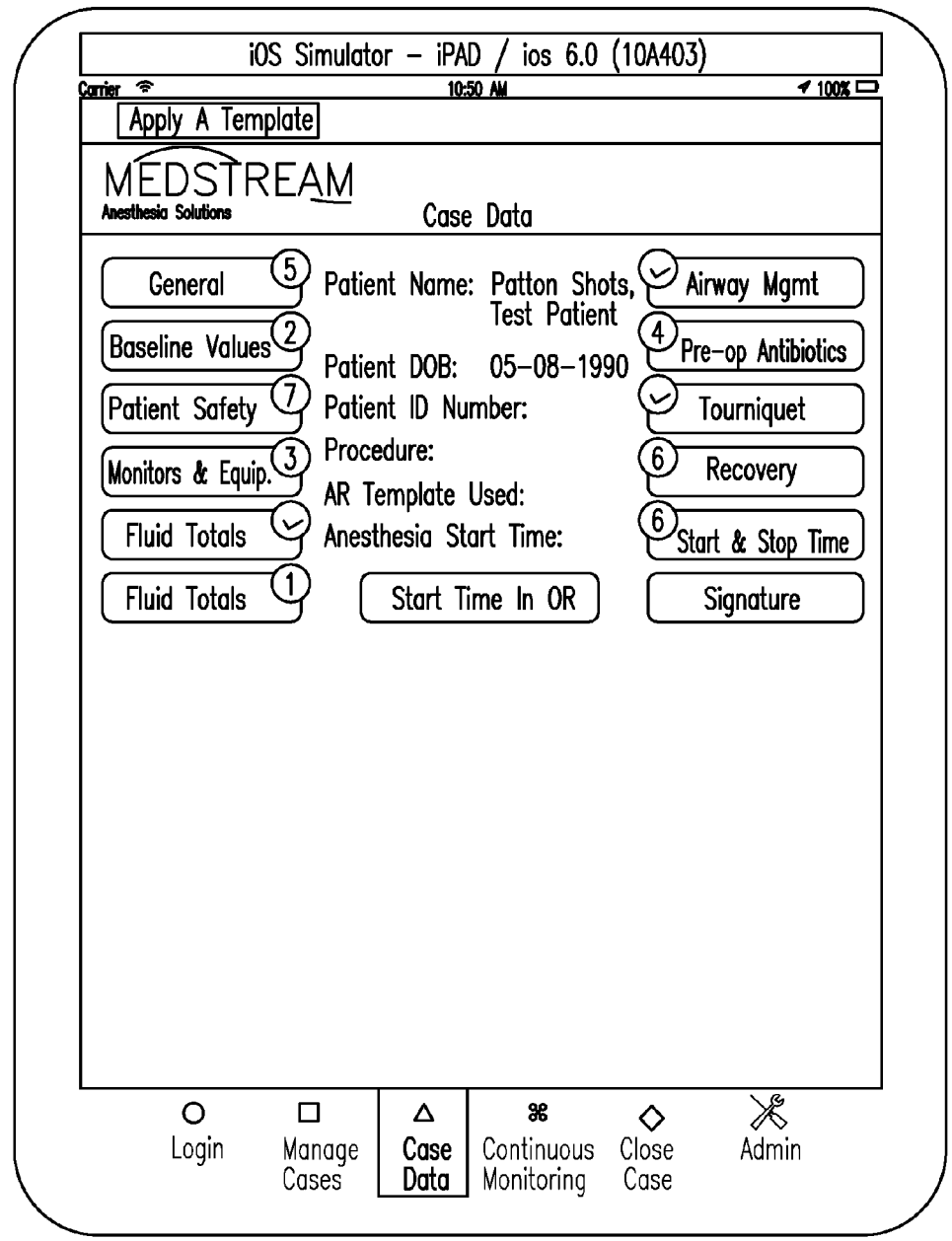
FIG. 5 depicts an exemplary procedure module interface in accordance with an exemplary embodiment of present disclosure.

FIG. 5 provides an exemplary anesthesia record module interface 244. The module interface 244 allows a user to access or interact with the anesthesia record module 206. The module 206 can be accessed after the completion of modules 202, 204, and if applicable 216. While the anesthesia record module interface 244 is presented on the display of the computing device, a user can chart and/or monitor the patient throughout the procedure. In one embodiment, the user can be the anesthesiologist managing the patient and/or overseeing the administration of anesthesia to the patient or a CRNA managing the patient. Some of the information required by the module 206 can be collected by accessing the patient's data collected from one or all of the previous modules.

For the exemplary embodiment of FIG. 5, the anesthesia record module 206 accesses an "eAR" submodule (shown in FIG. 5). It should be appreciated, however that in other exemplary embodiments, the anesthesia record module can access instead an "eOB" sub-module for birth and delivery specific anesthesia cases, an "eEndo" sub-module for endoscopy procedures, or an "eEyes" sub-module for eye procedures and general cataract removal. It should also be appreciated that in other exemplary embodiments, the eAR submodule can instead be a stand-alone module.

FIG. 6 provides an exemplary postoperative evaluation module interface 246. The module interface 246 allows a user to access or interact with the postoperative evaluation module 208. The module 208 can be accessed after the completion of modules 202, 204, 206, and if applicable 216. While the postoperative evaluation module interface 246 is presented on the display of the computing device, a user can collect data associated with the patient and the patient's recovery, such as, for example, the patient's postoperative conditions and vital signs. In one embodiment, the user can be the anesthesiologist managing the patient and/or overseeing the administration of anesthesia to the patient or a CRNA managing the patient. Additionally, some of the information required by the postoperative evaluation module 208 can be collected by accessing the patient's data collected from one or all of the previous modules.

FIG. 7 provides an exemplary AQI module interface 248. The module interface 248 allows a user to access or interact with the AQI module 210. The module 212 can be accessed after the completion of modules 202, 204, 206, 208, and if applicable 216. While the AQI module interface 248 is presented on the display of the computing device, a user can collect data to evaluate whether or not the administration of anesthesia went as planned and can note if there is any room for improvement in the administration of anesthesia to future patients. If the administration of anesthesia to the patient did not go as planned, the AQI module interface 248 can prompt the user to provide certain information prior to completing the AQI module 210. In one embodiment, the user can be the anesthesiologist managing the patient and/or overseeing the administration of anesthesia to the patient. Additionally, some of the information required by the AQI module 210 can be collected by accessing the patient's data collected from one or all of the previous modules.

Figure 8:
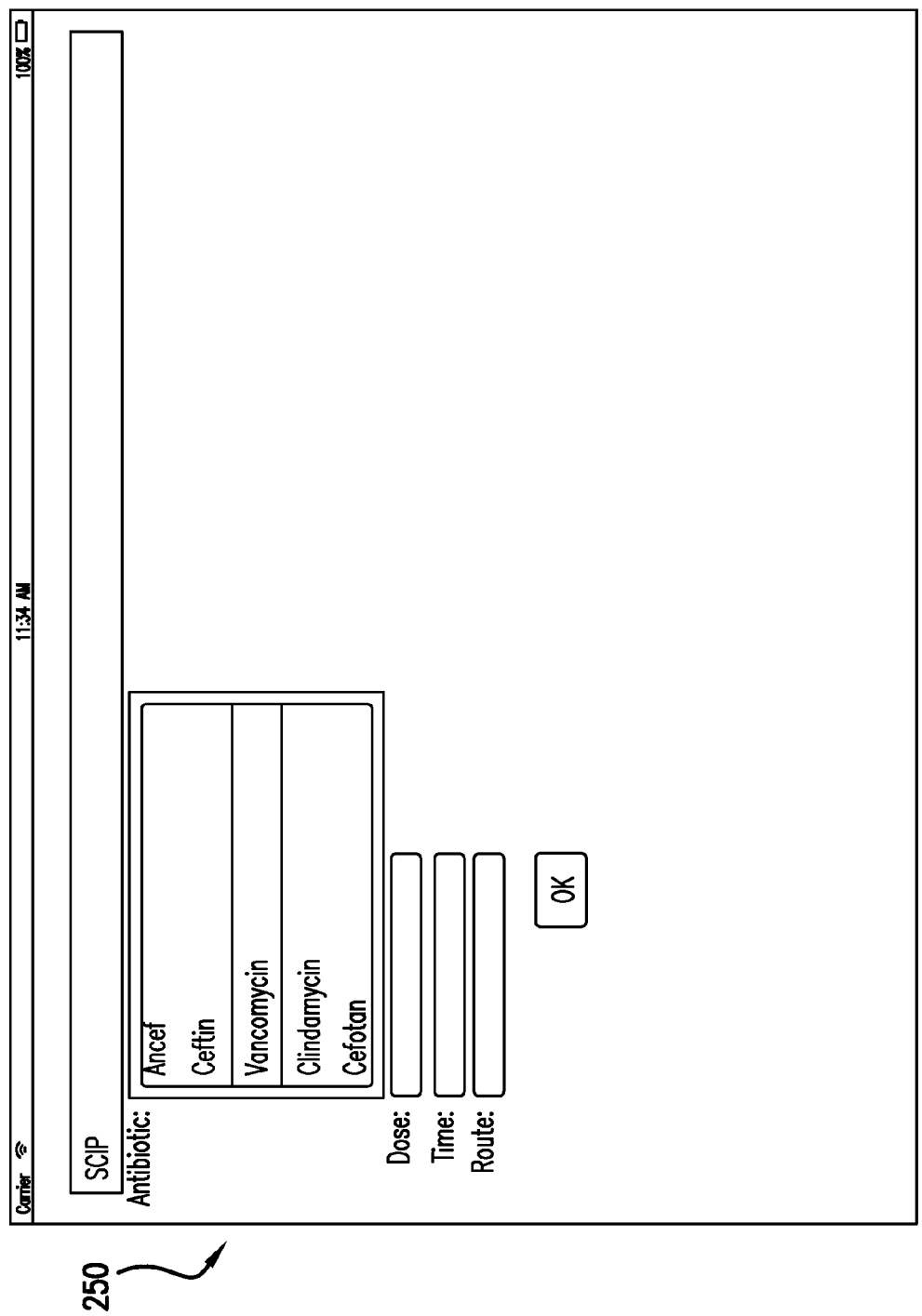
FIG. 8 depicts an exemplary anesthesia quality improvement module interface in accordance with an exemplary embodiment of present disclosure.

FIG. 8 provides an exemplary SCIP evaluation module interface 250. The module interface 250 allows a user to access or interact with the SCIP evaluation module 212. The module 212 can be accessed after the completion of modules 202, 204, 206, 208, 210, and if applicable 216. While the SCIP evaluation module interface 250 is presented on the display of the computing device, a user can collect data to evaluate whether or not certain government requirement and/or certain hospital or health care provider policies have been complied with. In one embodiment, the user can be the anesthesiologist managing the patient and/or overseeing the administration of anesthesia to the patient. Such an embodiment can ensure compliance with certain policies and/or government requirements prior to closing the case. Additionally, some of the information required by the SCIP evaluation module 212 can be collected by accessing the patient's data collected from one or all of the previous modules.

FIG. 9 provides an exemplary patient satisfaction report module interface 252. The module interface 252 allows a user to access or interact with the patient satisfaction report module 214. Module 214 can be accessed after the completion of modules 202, 204, 206, 208, 210, 212, and if applicable 216. While the patient satisfaction report module interface 252 is presented on the display of the computing device, a user can collect data to determine the patient's level of satisfaction with the administration of anesthesia. In one embodiment, the user can be an anesthesiologist (not necessarily the one managing the patient and/or administering the anesthesia to the patient), a CRNA, an administrative person, or the patient. Additionally, some of the information required by the patient satisfaction report module 214 can be collected by accessing the patient's data collected from one or all of the previous modules.

FIG. 10 provides an exemplary nerve block module interface 254, accessing the nerve block module 216. Module 216 can be accessed after the completion of module 202 if it is anticipated that the patient may need additional pain prevention measures. While the nerve block module interface 254 is presented on the display of the computing device, a user can collect data relevant to the administration of a nerve block. In one embodiment, the user can be the anesthesiologist managing the patient and/or administering the anesthesia to the patient. Additionally, some of the information required by the nerve block module 216 can be collected by accessing the patient's data collected from one or all of the previous modules.

It should be appreciated, however, that the sequential order of the plurality of modules presented in the dashboard view 200 is by way of example only. In other exemplary embodiments, the dashboard view 200 can present the plurality of modules in any suitable sequential order determined to promote efficient collection of the required anesthesia perioperative data. For example, the nerve block module 216 could be presented after the preoperative assessment module 202. Additionally, it should be appreciated that the specific modules presented are also by way of example only. In other exemplary embodiments, any suitable number of modules may be included so as to effectively collect the patient's anesthesia perioperative data from the preoperative period, the interoperative period, and the postoperative period of the patient's procedure. For example, certain of the modules in the exemplary embodiment of FIGS. 2-10 could be combined into a single module, or alternatively could be divided into two or more separate modules.

Method for Collecting and Managing Anesthesia Perioperative Data

Figure 11:
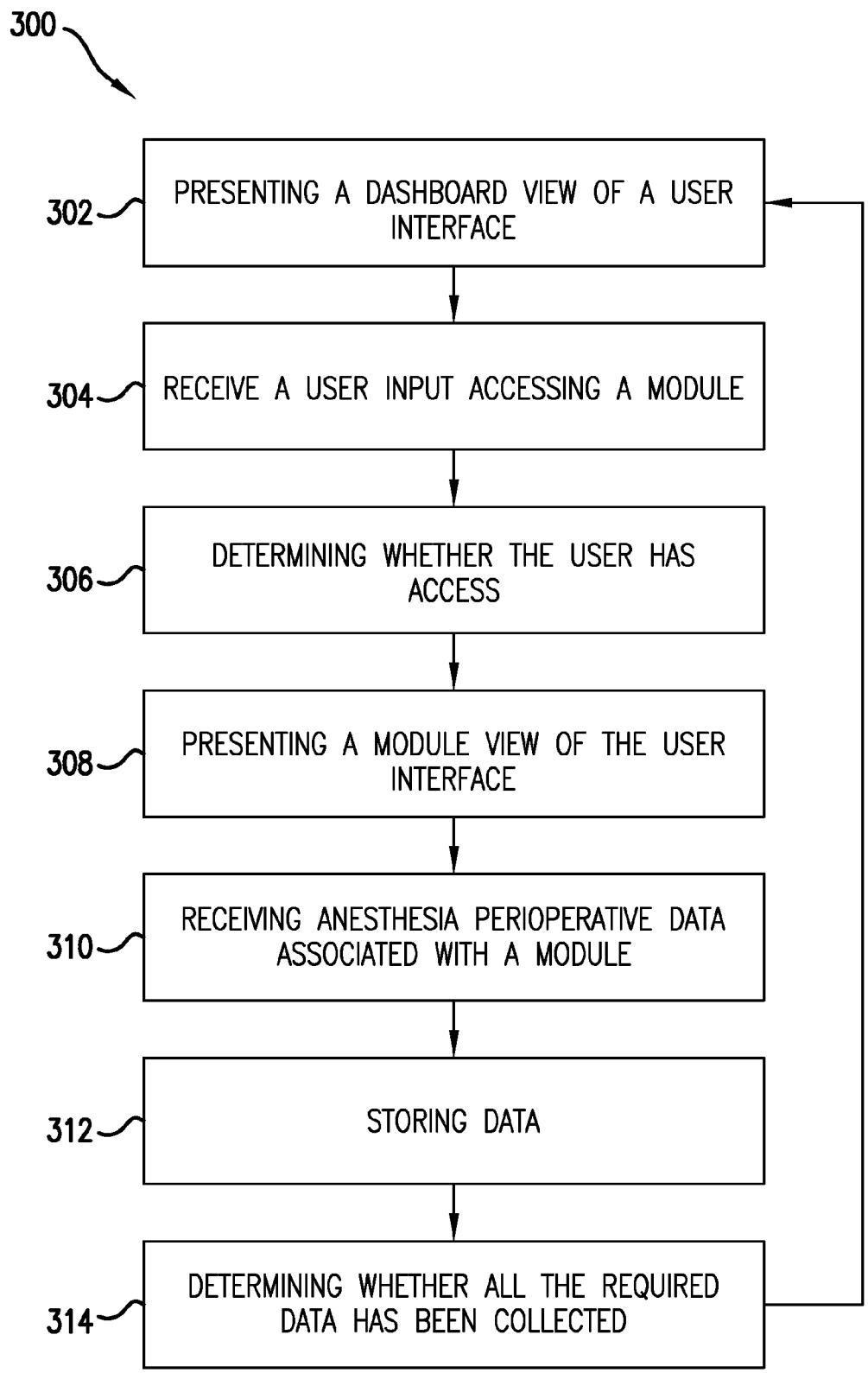
FIG. 11 depicts a flow diagram of an exemplary method according to an exemplary embodiment of the present disclosure.

Referring now to FIG. 11, a flow diagram is provided illustrating an exemplary computer-implemented method (300) for collecting and managing anesthesia perioperative data of the patient. In the exemplary method (300), a dashboard view of a user interface is presented at (302). The dashboard view of the user interface can be presented on the display the computing device, which in one exemplary embodiment can be a touch screen display of a handheld computing device. Additionally, the user interface can display a plurality of modules in a sequential order. Each of the modules can correspond to various perioperative periods of the patient's procedure. A specific discussion of an exemplary dashboard view and an exemplary sequence of modules can be found in the previous section, with reference to FIGS. 2-10.

As shown in FIG. 11, the exemplary method (300) includes receiving a user input at (304) accessing a module in the plurality of modules. Such a user input can be a touch interaction with the display of the computing device. In response to the user input at (304), the exemplary method (300) at (306) includes determining whether the user has access to the module based on the completion of one or more previous modules in the sequential order in which plurality of modules are displayed in the dashboard view. For example, if the user is attempting to access the third module presented in the dashboard view at (302), the method (300) at (306) will include determining whether the previous two modules have been completed. Notably, if the user is attempting to access the first module in the plurality of modules, then at (306) the method (300) will include determining that the user has access to the module, as there would be no previous modules that were incomplete.

If it is determined at (306) that the user has access to the module corresponding to the user input at (304), then a module interface associated with and accessing the first module is presented at (308). The module interface presented at (308) is unique to the module selected. Additionally, once the module interface is presented at (308), the method (300) includes at (310) receiving anesthesia perioperative data of the patient associated with the perioperative period corresponding to the particular module. The data received at (310) can be input using any suitable means, such as by a user's touch interaction with the display of the computing device. In one exemplary embodiment, the user can be an anesthesiologist, a CRNA, an administrative person, the patient, or any other suitable person based on the data required to be collected. As the data is received at (310), the method (300) can include storing the data in a memory at (312). In one exemplary embodiment, the memory can be an internal memory of the computing device, or in another exemplary embodiment, the data can be communicated to and stored by a remote server.

Once all of the required anesthesia perioperative data of the patient required by the module has been received at (310) and stored at (312), the method includes determining that all the required data has been entered at (314). In certain exemplary aspects of method (300), determining that all the required data has been entered at (314) can further include verifying that the anesthesia perioperative data required by the selected module has been entered. Additionally, in other exemplary aspects, the method (300) can include providing a signal indicative of receipt of all required anesthesia perioperative data of a patient associated with the completed module. By way of example, the signal can be an indicia on the display of the computing device, or can be a prompt provided on the display of the computing device.

As indicated in FIG. 11, once the method (300) has determined that all required data has been received at (314), the method can again include presenting the dashboard view 200 of the user interface at (302)-(304) through (314) can then be repeated until each module in the plurality of modules has been completed.

In one exemplary aspect, the method (300) can additionally include presenting a plurality of indicia in the dashboard view at (302). In such an embodiment, each indicia in the plurality of indicia presented can correspond to a module in the plurality of modules. Additionally, each indicia can indicate whether the corresponding module has been determined to be complete at (314). For example, each indicia can include a colored portion of the corresponding module, wherein the color of the colored portion is indicative of whether the module has been determined to be complete at (314) (e.g., the colored portion may be green if the module has been determined to be complete, and can be red if the module has not been determined to be complete). In such an embodiment, the colored portion could comprise a portion extending around a periphery of each of the modules presented in the dashboard view of the user interface at (302).

Figure 12:
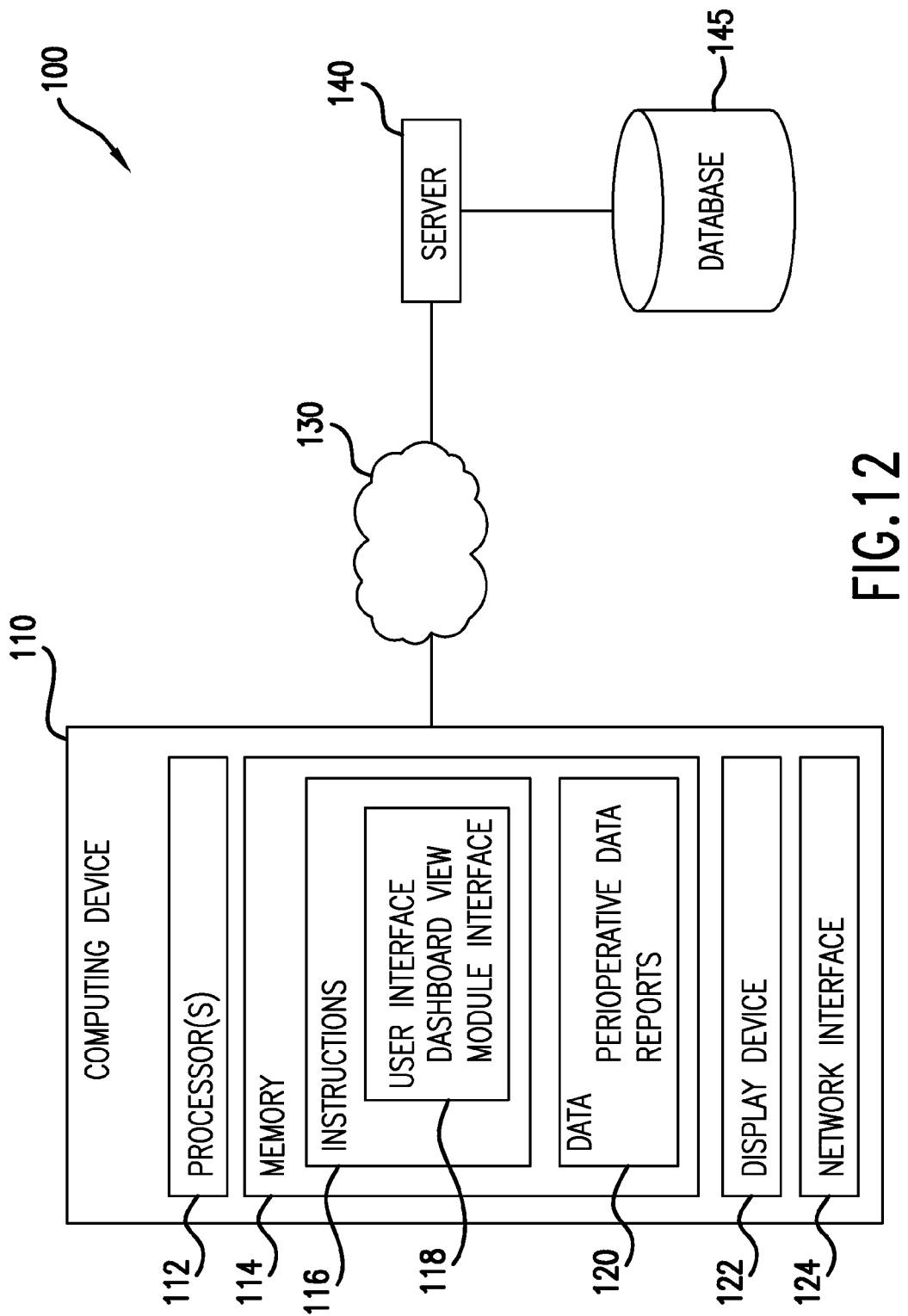
FIG. 12 depicts an exemplary computer-based system according to an exemplary embodiment of the present disclosure.

It should be understood that the exemplary method of FIG. 11 can be implemented using any suitable computing system, such as the computing system depicted in FIG. 12. In addition, FIG. 11 depicts the method (300) being performed in a particular order for purposes of illustration and discussion. Those of ordinary skill in the art, using the disclosures provided herein, will understand that various steps of the methods discussed herein can be omitted, rearranged, combined and/or adapted in various ways.

Exemplary Computer Based System for Collecting Anesthesia Perioperative Data

FIG. 12 depicts an exemplary computing system 100 that can be used to implement the systems and methods for collecting and managing anesthesia perioperative data of a patient according to exemplary aspects of the present disclosure. The system 100 includes a computing device 110. The computing device 110 can include a general purpose computer, special purpose computer, laptop, desktop, smartphone, tablet, cell phone, mobile device, integrated circuit, or other suitable computing device.

The computing device 110 can have a processor(s) 112 and a memory 114. The computing device 110 can also include a network interface 124 used to communicate with remote computing devices over a network 130. In one exemplary implementation, the computing device 110 can be in communication with a server 140, which can also be in communication with a billing system, a health care management system, etc. (not shown).

The processor(s) 112 can be any suitable processing device, such as a microprocessor, microcontroller, integrated circuit, or other suitable processing device. The memory 114 can include any suitable computer-readable medium or media, including, but not limited to, RAM, ROM, hard drives, flash drives, magnetic or optical media, or other memory devices. The memory 114 can store information accessible by processor(s) 112, including instructions 116 that can be executed by processor(s) 112. The instructions 116 can be any set of instructions that when executed by the processor(s) 112, cause the processor(s) 112 to perform operations. For instance, the instructions 116 can be executed by the processor(s) 112 to implement the exemplary user interface 102. As discussed, the user interface 102 can allow a user of the computing device 910 to more efficiently and intuitively collect and manage anesthesia perioperative data of a patient throughout the patient's procedure.

Memory 114 can also include data 118 that can be retrieved, manipulated, created, or stored by processor(s) 112. For instance, memory 114 can store anesthesia perioperative data associated with one or more patients, data associated with reports of the collected anesthesia perioperative data, etc.

It should be appreciated, that the term "engine" or "module" as used herein, refers to computer logic utilized to provide desired functionality. Thus, an engine or module can be implemented in hardware, application specific circuits, firmware and/or software controlling a general purpose processor. In one embodiment, the engines or modules are program code files stored on the computing device 110, loaded into a memory and executed by a processor, or can be provided from computer program products, for example computer executable instructions, that are stored in a tangible computer-readable storage medium such as RAM, hard disk or optical or magnetic media.

Computing device 110 can include or can be coupled to one or more input/output devices. Input devices may correspond to one or more peripheral devices configured to allow a user to interact with the computing device. One exemplary input device can be a touch interface (e.g. a touch screen or touchpad) that allows a user to interact with the exemplary user interface using touch commands. Output device can correspond to a device used to provide information to a user. One exemplary output device includes a display 122 of a handheld computing device, such as the display of a tablet computer. The computing device 110 can include or be coupled to other input/output devices, such as a keyboard, microphone, mouse, audio system, printer, and/or other suitable input/output devices. Additionally, the computing device 110 can include or be coupled with monitoring devices, such as those that may be used to monitor a patient during an aspect of a procedure.

The server 140 can host the data collection and management system. The server 140 can be configured to exchange data with the computing device 110 over the network 130. For instance, responsive to a request for information, the server 140 can encode data in one or more data files and provide the data files to the computing device 110 over the network 130. Similar to the computing device 110, the server 140 can include a processor(s) and a memory. The server 140 can also include or be in communication with one or more databases 145. Database(s) 145 can be connected to the server 140 by a high bandwidth LAN or WAN, or can also be connected to server 140 through network 130. The database 145 can be split up so that it is located in multiple locales.

The network 130 can be any type of communications network, such as a local area network (e.g. intranet), wide area network (e.g. Internet), or some combination thereof. The network 530 can also include a direct connection between a computing device 110 and the server 140. In general, communication between the server 140 and a computing device 110 can be carried via network interface 124 using any type of wired and/or wireless connection, using a variety of communication protocols (e.g. TCP/IP, HTTP, SMTP, FTP), encodings or formats (e.g. HTML, XML), and/or protection schemes (e.g. VPN, secure HTTP, SSL).

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A mobile computing device comprising a display device, one or more processors, and at least one tangible non-transitory computer-readable medium, the computer-readable medium storing instructions that when executed by the one or more processors cause the one or more processors to perform operations, the operations comprising:
   presenting a dashboard view of a user interface on a display of a computing device, the dashboard view displaying a plurality of modules, wherein the plurality of modules are displayed in a sequential manner corresponding to a sequential order of perioperative periods;
   receiving a user input accessing a first module of the plurality of modules, the first module configured to receive anesthesia perioperative data of a patient;
   in response to the user input, determining whether the user has access to the module based on completion of one or more previous modules in the sequential order;
   presenting a first module interface associated with the first module when it is determined that the user has access to the first module;
   receiving anesthesia perioperative data of the patient associated with the first module;
   determining that all required anesthesia perioperative data of the patient associated with the first module has been received; and
   providing a signal indicative of receipt of all required anesthesia perioperative data of a patient associated with the first module.

2. The mobile computing device of claims 1, wherein the plurality of modules include at least a preoperative evaluation module, an immediate preinduction evaluation module, a procedure module, a postoperative evaluation module, a surgical care improvement plan evaluation module, an anesthesia quality improvement module, and a patient satisfaction report module, and wherein the plurality of modules are displayed in the dashboard view in the following order and must be completed in the following order: first the preoperative evaluation module, second the immediate preinduction evaluation module, third the procedure module, fourth the postoperative evaluation module, fifth the anesthesia quality improvement module, sixth the surgical care improvement plan evaluation module, and seventh the patient satisfaction report module.

3. The mobile device of claim 1, wherein the operation of determining that all required anesthesia perioperative data of the patient associated with the first module has been received such that the first module is complete further comprises verifying that the anesthesia perioperative data required by the first module has been entered.

4. The mobile device of claim 1, wherein the dashboard view of the user interface further comprises a plurality of indicia corresponding to each module in the plurality of modules, wherein the plurality of indicia indicate whether or not the corresponding module has been determined to be complete.

5. The mobile device of claim 4, wherein the plurality of indicia comprise a colored portion of the corresponding module presented in the dashboard view of the user interface, wherein the color of the colored portion is indicative of whether or not the module has been determined to be complete.

6. The mobile device of claim 1, wherein the mobile device is a handheld mobile computing device.

7. The mobile device of claim 1, wherein the user input is a touch interaction with the mobile device.

8. The mobile device of claim 1, wherein the operations further comprise:
   accessing information associated with a user;
   determining whether the user has authorization to access the case as a manager.

9. The mobile device of claim 8, wherein the operations further comprise:
   changing information associated with the user such that a new party has access to the case as a manager.

10. The mobile device of claim 1, wherein the operations further comprise:
    providing one or more reports based on the anesthesia perioperative data of the patient associated with the case.

* * * * *